United States Patent [19]
Baum et al.

[11] Patent Number: 5,361,284
[45] Date of Patent: Nov. 1, 1994

[54] TUBE CORROSION ACCELERATOR

[75] Inventors: Allen J. Baum, Pittsburgh, Pa.; William M. Cox, Cheshire, England

[73] Assignee: Westinghouse Electric Corporation, Pittsburgh, Pa.

[21] Appl. No.: 26,047

[22] Filed: Mar. 4, 1993

[51] Int. Cl.$^5$ .............................................. G21C 17/00
[52] U.S. Cl. ................... 376/245; 376/305; 73/86; 73/865.6; 422/53
[58] Field of Search .............. 376/245, 260, 305, 463; 73/86, 865.6; 422/53; 436/6; 434/218

[56] References Cited
U.S. PATENT DOCUMENTS
4,637,346  1/1987  Draper et al. ................ 73/865.6

*Primary Examiner*—Daniel D. Wasil

[57] ABSTRACT

A device for creating a corrosive condition and monitoring that condition, adapted for use in active fluid heat exchangers, has a sealed tube having corrosion sites spaced apart on its exterior. Structure positioned on the outside of the tube at the corrosion sites provide crevices for retaining corrosive sludges in contact with the corrosion sites. The interior of the tube is pressurized with a gas to stress the tube thereby accelerating corrosion of the surface. Heat is provided to the corrosion sites from within the tube when placed within a fluid reservoir, such as the secondary side of a fluid heat exchanger. The heat concentrates corrosive chemicals at the corrosion sites, also accelerating corrosion. Electronic probes can be mounted in proximity to the corrosion sites for real time monitoring of the progress of corrosion.

21 Claims, 5 Drawing Sheets

TUBE CORROSION ACCELERATOR

BACKGROUND OF THE INVENTION

1. Technical Field

This invention relates to a class of devices for creating a range of corrosive conditions simulating those found in crevices of metal surfaces contained within a corrosive medium. It has particular application to the conditions found in heat exchangers, especially at the surfaces of heat exchange tubes within the secondary side of pressurized water reactor nuclear steam generators.

This invention additionally relates to methods of monitoring and predicting tube crevice corrosion, also having applications to the operation of heat exchangers.

2. Description of the Prior Art

The thin-walled metal tubes that are generally used in heat exchangers often suffer highly stressed conditions during extended periods of use. Stresses caused by elevated temperatures and pressures in combination with a corrosive chemical environment can lead to failure of these metals. This process occurs frequently at the crevices formed at interfaces with supporting structures. Corrosive debris suspended in a heat exchanger fluid can accumulate in the crevices as a corrosive sludge. Where a heat exchanger contains a hazardous material, or where the heat exchanger is within a system that is difficult or costly to shut down for maintenance, it is especially important to be able to monitor corrosive degradation, or even better, to predict catastrophic failure before it happens. Environmental concerns and cost considerations are both important in pressurized water reactor (PWR) nuclear steam generators.

Because corrosion of the heat exchanger tubes of PWR steam generators present special concerns related to this invention, it is worthwhile to outline some of the details of these systems. Nuclear powered steam generators have three principle parts. A primary side contains radioactive hot water heated by the nuclear core. A secondary side contains non-radioactive water which, upon being converted into steam, powers the turbine generator. Heat is transferred from the primary side to the secondary side by a heat exchanger comprising a tube sheet in which the inlet and outlet ends of a plurality of U-shaped tubes are mounted. In PWR's, water from the primary side enters the U-shaped tubes through the inlets, flows through the U-shaped tubes and exits the outlets which are hydraulically isolated from the inlets by a divider sheet. A second hydraulic flowpath circulates non-radioactive water around the outside surfaces of the U-shaped tubes extending into the secondary side. Heat from the primary side is transferred across the metal boundaries of the U-shaped tubes to the secondary side.

The U-shaped heat exchange tubes of nuclear powered steam generators are subjected to conditions which can lead to corrosion and failure of the tubes. Corrosion in the crevice regions of the heat exchanger is especially troublesome. Crevices are formed in the annular space between the heat exchange tubes and the tube sheet and also in the annular clearance between the tubes and the support plates in the secondary side. The support plates are used to uniformly space and align these tubes which otherwise would be buffeted about by the strong hydraulic flow around them. A sludge formed of particulates in suspension in the secondary side tends to collect in these crevices. These sludges are comprised predominantly of iron oxides and copper. The normal hydraulic circulation of the water in the secondary side is not sufficient to flush out the sludge from these crevices. In fact, the poor hydraulic circulation in these regions exacerbates the situation. The collection of sludge in the crevices impedes heat transfer from these regions, creating localized areas of elevated temperature (or "hot spots") in the tubes adjacent the sludge. The elevated temperatures in the "hot spots" allow higher local concentrations of corrosive impurities in solution, accelerating the corrosion process. Nuclear power plant operators periodically attempt to sweep the sludge out of the generator vessel by hydraulic means, however this is not always effective. The U-shaped heat exchange tubes of nuclear steam generators are typically formed from corrosion resistant nickel alloys, such as Inconel ® 600, but corrosion in the crevices due to the elevated heat conditions and the high pressures found within the U-shaped tubes may ultimately penetrate the tube wall, resulting in leakage of radioactive water from the primary side into the non-radioactive water in the secondary side of the steam generator. Remedial action taken during maintenance shutdowns of the reactor can prevent such leakage, however it would be very useful to be able to know when corrosion is occurring before there is significant propagation.

While early forms of steam generator corrosion (thinning and denting) could be readily related to a particular operating chemistry, more recent forms of corrosion (intergranular corrosion and cold leg thinning) usually cannot be related to a direct cause. As impurity levels in steam generators have been reduced, it has become progressively more difficult to correlate contaminant levels, as measured either in the steam generator blowdown during power operation or by monitoring the hideout return following a shutdown, with the severity of corrosion, as measured by the time period required to initiate corrosion, its subsequent propagation rate, and the number of affected tubes. Because of the inability of using the operating chemistry as a means of judging the possible future extent of corrosion, a more direct means of relating a particular operating chemistry to the future occurrence of corrosion is highly desirable. With such a capability, it would be possible to undertake a corrective action well in advance of the corrosion actually occurring.

For this reason, model steam generators were developed to monitor the corrosion occurring in the heat exchange tubes of particular steam generators so that corrective action could be taken before failure of the tube walls. Model steam generators are bulky complicated apparatuses that attempt to mimic the actual steam generators. They contain all the hydraulic elements of an actual steam generator including circulating primary water, circulating secondary water and heat exchange tubes. They operate by subjecting an array of sample heat exchange tubes to a set of heat, pressure and chemical conditions approximating that which surrounds the heat exchange tubes in such nuclear steam generators. Their accuracy depends upon the accuracy of the simulation of the conditions within the operating steam generator. One type of model steam generator is described in U.S. Pat. Nos. 4,628,870, 4,635,589 and 4,640,233, all which were assigned to the Westinghouse Electric Corporation. A more compact model steam generator was disclosed in U.S. Pat. No. 4,637,346, also assigned to the Westinghouse Electric Corporation.

Model steam generators, while being useful instruments for simulating conditions in an actual steam generator, do not subject the tubes in the model steam generators to exactly the same conditions as found in an operating generator. Although the same secondary side feedwater source as used in a PWR generator may be fed into the model generator's secondary side, this does not guarantee the same chemistry as that found within the power plant's secondary side. An additional defect they suffer is that it is difficult to change the primary tubes in the model steam generators, for example, to do inspection or destructive testing of the heat exchange tubes.

SUMMARY OF THE INVENTION

There exists a need for a simpler system which can monitor the actual corrosive degradation of heat exchanger tubes. There is also a need for a system that can accurately monitor corrosion.

Accordingly, it is an object of the present invention to provide an apparatus for creating a range of corrosive conditions as found in fluid heat exchanger tubing.

It is another object of this invention to provide an apparatus that is capable of monitoring tube corrosion within an operating heat exchanger.

A further object of this invention is to provide an apparatus for predicting tube corrosion within an operating heat exchanger.

It is an object of this invention to provide an apparatus for monitoring and predicting heat exchanger tube corrosion within operating PWR steam generators without interfering with the operation of the reactor.

It is an object of this invention to provide a simplified, light-weight heat exchanger tube corrosion monitor and predictor.

It is an object of this invention to provide a method for identifying and characterizing steam generator tube support plate crevice corrosion before it occurs in active heat transfer tubing without removing an active tube from the steam generator.

These objects and others that will become more readily apparent are obtained in accordance with this invention. The present invention is a device for creating a corrosive condition on the exterior surface of an elongated sealed metal tube, such as those used in heat exchangers, and more particularly those used in PWR's. The device has means, such as a gas inlet port, for pressurizing the interior of the tube, and also has a heating means for providing heat to a predetermined position within the tube. Disposed exterior to the tube is a structure for retaining a corrosive medium in contact with the exterior of the tube proximate to the predetermined position.

In one version of this device, the structure for retaining a corrosive medium in contact with the exterior surface of the tube is provided by a member simulating a tube support plate in a heat exchanger. The member, positioned approximately adjacent to the exterior surface of the tube, provides a crevice for trapping a corrosive sludge as found in the heat exchangers of PWR's. In another version, it is provided by a porous, consolidated material. A water-based solution having corrosive components can interpenetrate the porous material, simulating a sludge in a crevice. In either case, the purpose is to simulate the conditions in actual heat exchangers, wherein the heat exchange tubes are supported and held in place by structures that allow the collection of sludges in crevices at the surfaces of the tubes.

Another aspect of this invention is that the device indicates corrosion taking place in an operating heat exchanger, thereby allowing an operator to take remedial measures before a leak occurs. This function is especially important for the heat exchangers of PWR's, where even a small leak of radioactive water (about 20 9 pm) from the primary side to the secondary side can cause the shutdown of the power plant. The device is adapted to be inserted into an active fluid heat exchanger, close to the heat exchange tubes or in an adjacent vessel. A measuring probe for providing a first signal indicative of a corrosion condition of the exterior surface of the tube proximate to the structure for retaining a corrosive medium allows in situ monitoring of the progress of tube corrosion conditions.

The invention includes a method for creating corrosion of surfaces and monitoring that corrosion. The method allows for the creation of conditions similar to those found at the surfaces of U-tubes in heat exchangers having primary and secondary sides. The method uses an apparatus comprising an elongated sealed tube having an exterior surface, a heating source for providing heat to the tube at a first axial position within the tube, structure for retaining a corrosive medium, such as the sludge deposits found in the crevices between the U-tubes and support plates, in contact with the exterior surface proximate to the first axial position, means for pressurizing the interior of the tube, and a measuring probe for providing a first signal indicative of a corrosion condition of the exterior surface proximate to the first axial position. The method includes the steps of: first placing a portion of the sealed tube comprising the structure for retaining a corrosive medium in contact with a corrosive medium, such as the secondary side of a heat exchanger in an active PWR; pressurizing the interior of the tube to a first pressure; heating the exterior surface of the tube proximate to the first axial position to a first temperature with the heating source; and then providing the first signal indicative of a corrosion condition with the measuring probe after pressurizing and heating the tube.

According to another aspect of this invention, a method is provided for creating corrosion of tube surfaces that is appropriate for monitoring heat exchangers. The method uses an apparatus comprising an elongated sealed tube, means within the tube for providing heat to the tube at a first axial position and for pressurizing the interior of the tube, and structure for retaining a corrosive medium in contact with the exterior surface of the tube proximate to the first axial position. First, a portion of the tube, comprising the structure for retaining a corrosive medium, is placed in contact with a corrosive medium. The interior of the tube at the first axial position is then heated and pressurized. Corrosion is enhanced by increasing the temperature and pressure. After a predetermined period of time, the temperature and pressure are reduced and the apparatus is removed from the corrosive medium. At this point, the tube can be examined for corrosion by nondestructive and/or destructive testing methods.

Either method is appropriate for use in active heat exchangers, adjacent pressure vessels or for laboratory testing. By adjusting the internal pressure of the tube to at least about the pressure experienced within active heat exchanger tubing, corrosion is accelerated. Corrosion is also accelerated by bringing the local temperature of the exterior surface in contact with the corrosive medium to a temperature at least about the temperature of an active heat exchanger tube. The corrosive medium may be provided by a bench-top setup wherein the chemistry of the medium can be adjusted by an operator. It may also be provided by an active heat exchanger, such as the secondary side of an active PWR steam generator. Using the first method, an operator monitoring the signal indicative of a corrosion condition can take corrective action well in advance of the occurrence of significant corrosion of actual heat exchanger tubing. The second method involves simpler equipment and can be used in conjunction with regular servicing shutdowns of PWR's.

BRIEF DESCRIPTION OF THE DRAWINGS

FIGS. 1 $a$, $b$ and $c$ display three embodiments of the corrosion accelerator of this invention.

DETAILED DESCRIPTION OF THE INVENTION

Figure 1A:
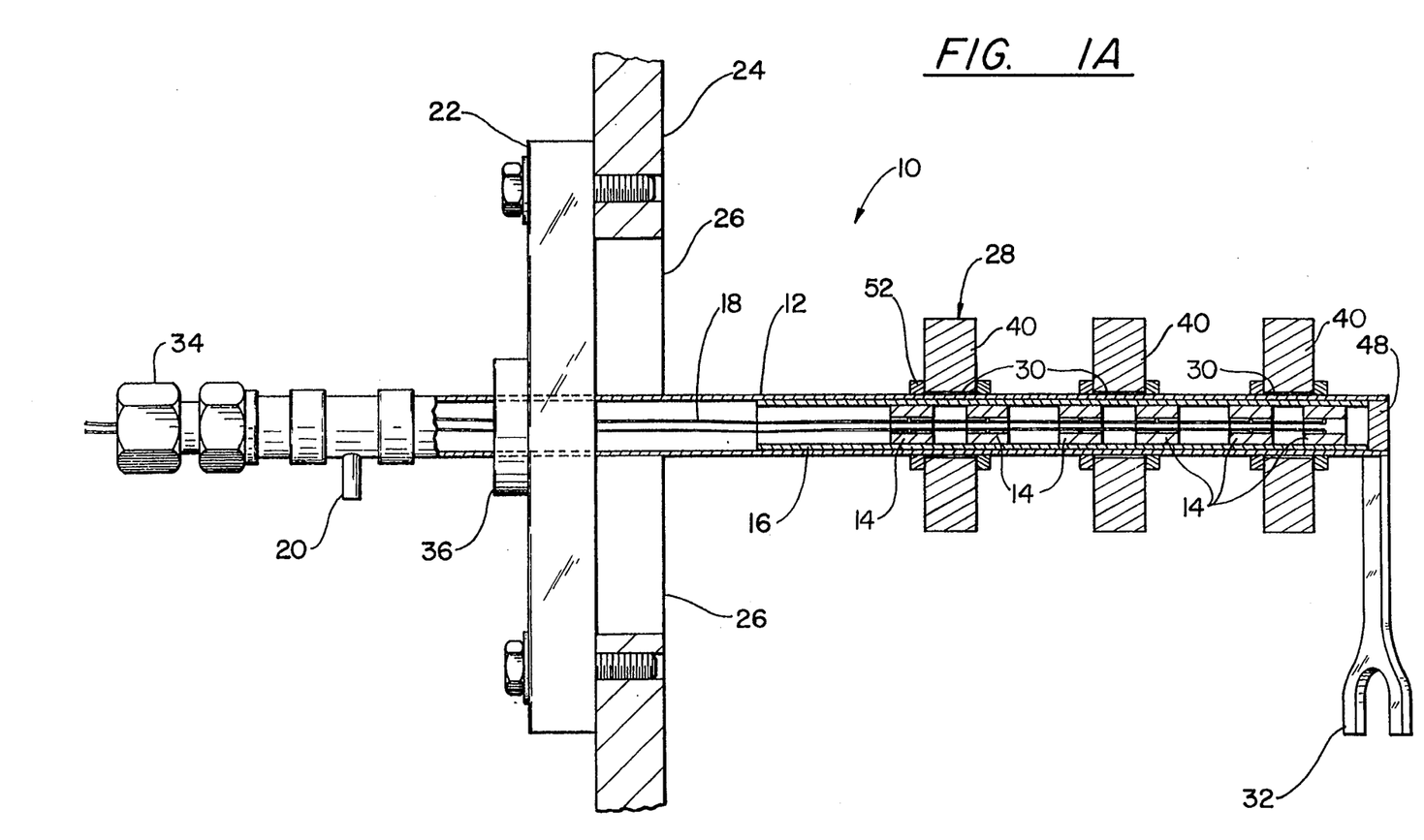
Figure 1B:
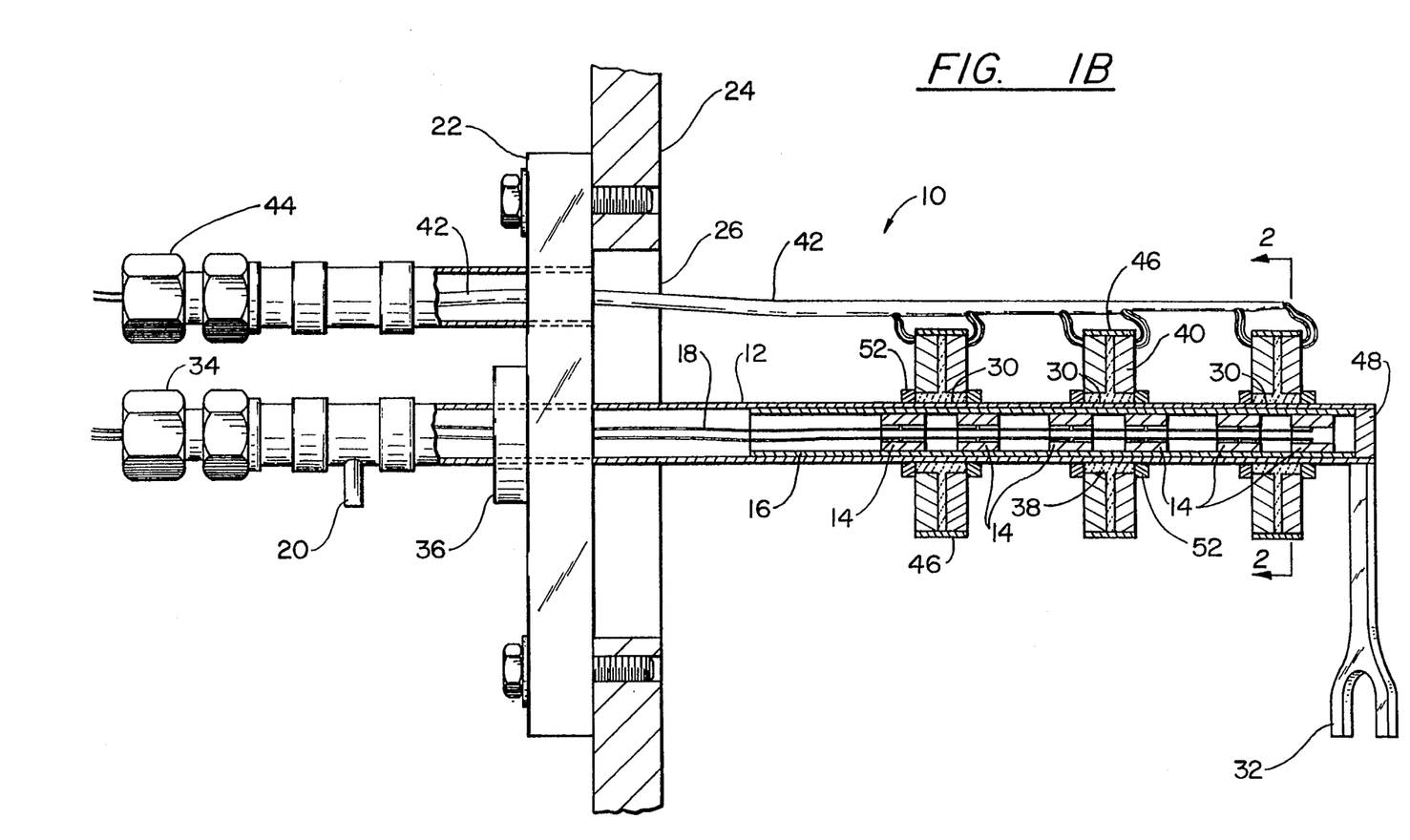
Figure 1C:
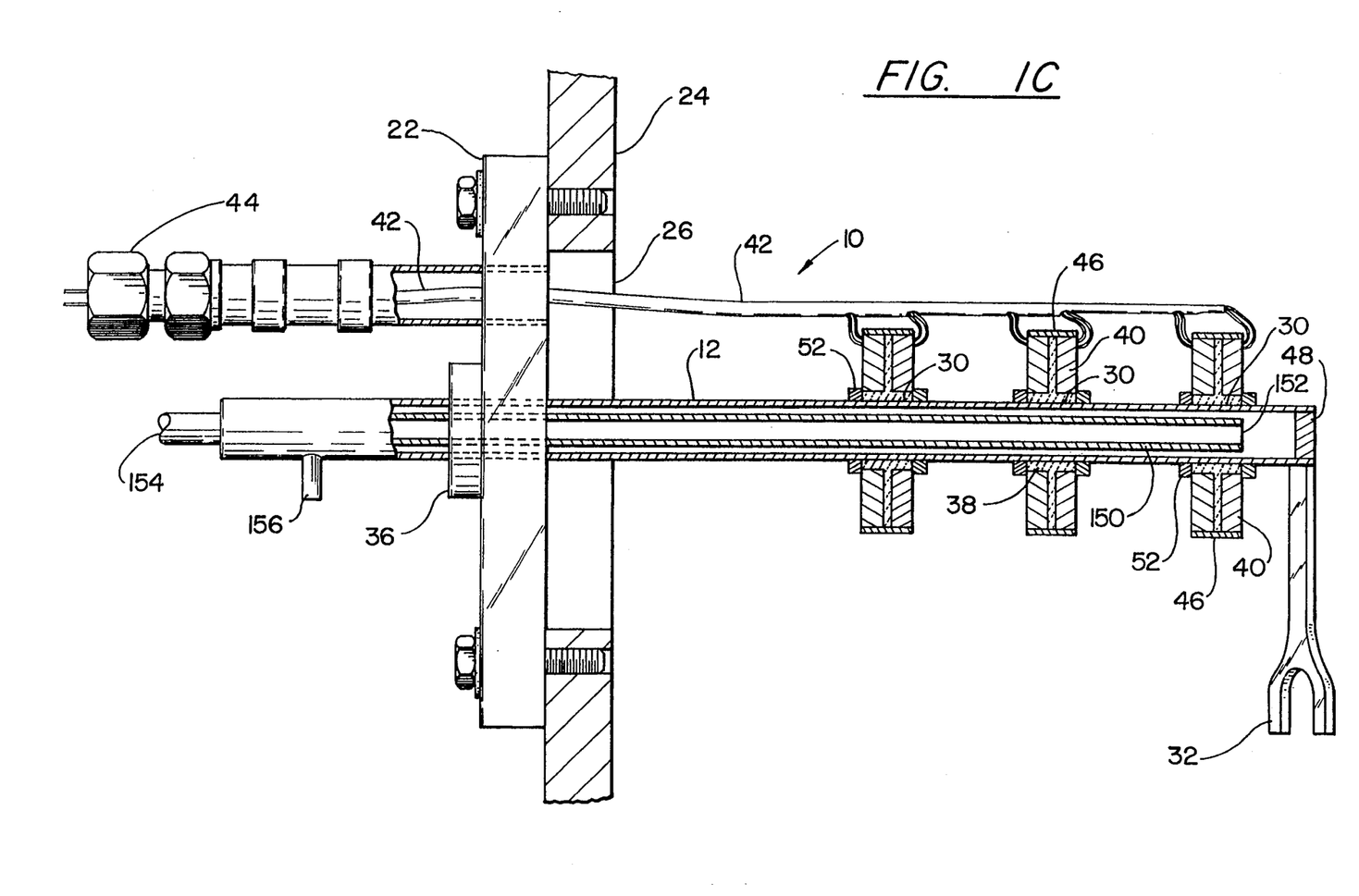

Referring to FIGS. 1 $a$, $b$ and $c$, displaying three embodiments of the corrosion accelerator adapted for use in the heat exchangers of PWR's, a tube 12 is provided of similar dimensions and composition as in a system whose heat exchange tubes are to be monitored. The U-tubes in PWR steam generators heat exchangers are typically $\frac{5}{8}"$–$\frac{7}{8}"$ in diameter. The exterior of the tube has a plurality of corrosion sites 30 spaced apart along its length.

Mounted on the exterior at the tube at the axial positions of the corrosion sites are structures for retaining a corrosive medium in contact with the exterior surface of the tube. One such structure is a member 28 that can be mounted either longitudinally or as an annular ring, as depicted in FIG. 1a. A corrosive sludge accumulates in the crevice 30 between the member and the exterior surface and also in the corners between their surfaces. The member may be made of the same material as support structures for heat exchange tubes in the heat exchanger to be monitored. In PWR's, the support plates for heat exchanger tubes are usually made of carbon steel or stainless steel. In a preferred embodiment, the member is an annular ring having a width of about $\frac{3}{4}$ inches and an outer diameter of about inches.

In another embodiment, depicted in FIGS. 1b and 1c, the structure for retaining a corrosive medium in contact with the exterior surface of the tube is a consolidated, porous medium 38. This medium is preferably the sludge that accumulates in the heat exchanger to be monitored or a material simulating the sludge. In PWR's the sludge comprises oxides of aluminum, zirconium, and iron, plus metallic copper. Therefore, a consolidated, metal oxide powder, such as a sinter of one or more of those materials, is preferred. This material serves as a medium for retaining a concentrated solution of dissolved chemicals that, in combination with the solution, simulates the sludge accumulations found in the operating heat exchangers of PWR's.

Also depicted in FIGS. 1b and 1c, mounted in close proximity to the structure for retaining a corrosive medium, are measuring probes 40 for monitoring corrosion conditions of the tube. Several different probes can be used to monitor the progression of corrosion of the sealed tube. The probes can be used to monitor at least some of the following characteristics of the tube indicative of corrosion conditions: potential noise, current noise, coupling current, zero resistance current, AC impedance and electrochemical potential. The probes 40 are shown to be electrically insulated from each other by insulator 50 and from the tube in FIG. 2 by the consolidated, porous medium 38. The probes may be shaped as annular rings or annular sections, as depicted. These annular structures are also $\frac{3}{4}$ inches wide and 2 inches in diameter.

Figure 2:
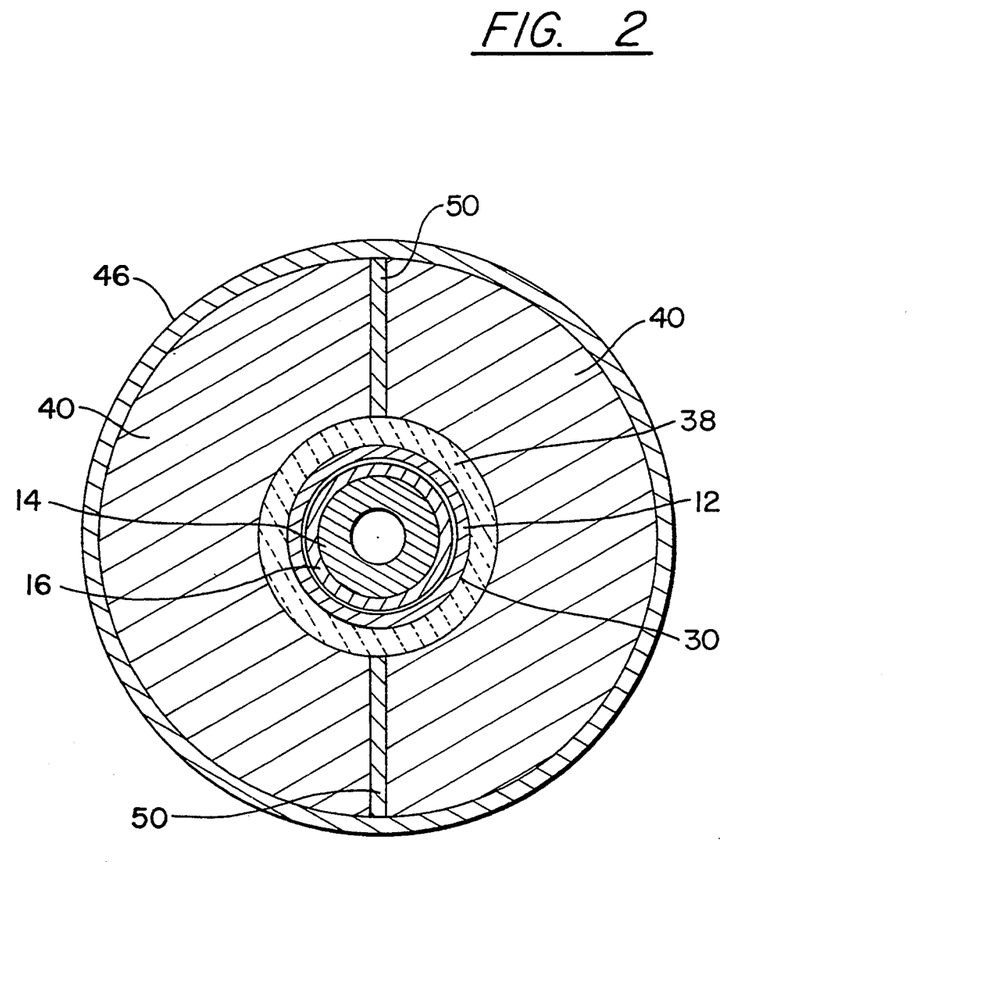
FIG. 2 displays a plan view of a probe assembly.

Probes can also be used in conjunction with other types of structures for retaining a corrosive medium, such as those depicted in FIG. 1a. In fact, properly shaped probes can themselves provide the structure for retaining a corrosive medium. It is important to note that the shape of the consolidated, porous medium 38, probes 40 or members 28 is not important, so long as the structure provides a means for retaining the corrosive medium in contact with the tube 12. The annular members 38 or the probes can be held in place at a fixed axial position with a variety of attachment means. Side brackets 52, designed so as to not block the crevice, such as the teflon brackets in FIG. 1, hold the annular structures in position with set screws. A strap 46, as depicted in FIG. 2, or some other means may be utilized to retain the probes and consolidated porous medium in together.

The data reduction software and hardware can be supplied by Capcis March, Ltd. of Manchester, England. The probes should be capable of directly monitoring the form and rate of corrosion of the tubing. The data reduction analysis techniques required to interpret the data generated by the probes are known in the art and are not included in this specification.

Positioned within the tube is a heater assembly. One type of heater assembly, depicted in FIGS. 1a and 1b, is constructed of a support tube 16 having an outer diameter slightly less than that of the inner diameter of the sealed tube. In a preferred embodiment, the annular gap between the tubes is about 0.025 inches. The support tube has positioned within it a heater at each of the axial positions of the corrosion sites. In this embodiment, each heater comprises a pair of electrical cartridge heaters 14 spaced about the corrosion site. A continuous hecter may also be used. The heaters are used to provide a superheat condition at each of the corrosion sites on the exterior of the tube which is comparable to or above that found on the hot leg side of the PWR steam generator. Typically, such temperatures are about 620° F. This will assure that chemicals are concentrated to the same levels in the Corrosion Accelerator as in the crevices of the heat exchanger. A spacing of less than about $\frac{1}{2}"$ between elements of a heater pair provides an almost uniform heat distribution around each of the corrosion sites. The cartridge heaters, which may be hollow as depicted in the figure, are held at fixed positions within the support tube by swaging down on the support tube at the heater sites, thereby clamping the support tube down on the heater at that site. The heaters can be plated with a high thermal conductivity metal, such as copper, to provide a uniform heat distribution about each cartridge heater. A thermocouple (not shown) positioned in the center of a heater can provide a reference temperature. The heater assembly, comprising the pairs of cartridge heaters 14, the support tube 16 and wire leads 18, is reusable.

The heater assembly is mounted toward a first end of the tube. The first end of the tube is sealed with a cap or end-plug 48, against which the heater assembly may abut. The heater wires 18 extend along to the opposite second end of the tube and exit through or terminate at a sealed fitting 34. In this embodiment, the fitting is a CONAX type fitting, which allows a simple feedthrough for the heater wires. The wires may then be connected to a heater control unit to provide power to the heaters.

Provided near the second end of the tube 12, opposite the heaters, is a gas inlet port 20. This allows connection to a source of pressurized gas. The interior of the tube 10 is a sealed chamber that will be pressurized with gas such that the internal pressure of the tube will be at least as high as the pressure corresponding to the fluid pressure on the primary side of the heat exchanger being monitored. For PWR's, this pressure is typically 2250 psi or above. Helium is the preferred pressurizing gas because of its high thermal conductivity and inert nature.

In another embodiment of the heater assembly, depicted in FIG. 1c, tube heating and pressurization is provided by a thermosiphon. In place of the cartridge heaters and helium gas source, the sealed tube has contained within it a smaller diameter inner tube 150 carrying steam. The inner tube has an opening 152 proximate to its termination point near the first end of the sealed tube. Its opposite end connects to an inlet port 154 near the opposite, second end of the sealed tube. Also near the second end, the sealed tube has an outlet port 156. High pressure steam enters the inner tube through the inlet port, flows through the inner tube and out through the opening near the termination point. The steam flows back through the annular space between the inner tube and the sealed tube, thereby heating the sealed tube. At least some of the steam condenses on the inner walls of the sealed tube, also providing heat to the tube. Condensates and steam exit the sealed tube through the outlet port. Gravity helps to drain condensates when the sealed tube is oriented vertically with its first end higher than its second end.

Since intergranular corrosion processes are a strong function of the tubing stress, the desired degree of corrosion acceleration can be established as a function of the initial tubing pressure. Laboratory testing can be performed to establish both the recommended heater power level and the helium backpressure to achieve the appropriate local chemical concentrations and desired degree of corrosion acceleration.

Each grouping of members 28 or sinter 38 with probes 40 about a crevice corrosion site comprises a crevice assembly. Depending upon the needs of the operator, the device may have a single type of crevice assembly or a variety. The simplest configuration has no probe means, and depicted in FIG. 1a. In this version, the members 28 provide crevices 30 for the corrosion sites. To monitor corrosion prior to tube failure, the tube must be removed from the heat exchanger for nondestructive or destructive testing. If probe means are used, as depicted in FIG. 1b, then corrosion can be monitored within an operating heat exchanger. In either case, an operator can vary the conditions for creating a corrosive condition by varying the temperature at the corrosion sites with the heaters and by varying the pressure stress within the tube with the gas pressure.

The tube 12 is mounted to a flange 22. The first end of the tube, having the heaters and the crevice corrosion sites, extends on a first side of the flange into the tubelane region of a heat exchanger. It may also be located elsewherein the steam generator, or in a vessel connected to the blowdown line. The second end of the tube, having the gas inlet port 20 and the sealed fitting for the electrical leads 18, extends on the opposite second side of the flange 22. A leak-tight seal to the flange is provided by a swage fitting 36. The first side of the flange mates with a port in the secondary side of the heat exchanger. The wire leads from the probes 42 extend through a probe lead port 44 provided on the flange. The probe lead port may also be provided with a CONAX type fitting. The flange mounts to a mating flange 24 providing a port 26 to the interior of a heat exchanger.

Depending upon the length of the tube, an anchor 32 may be provided on the first end of the tube, anchoring the tube to the blowdown line or tubesheet in the secondary side of the PWR steam generator. The anchor can reduce the risk of damage to the apparatus by buffeting from the strong hydraulic flow in the secondary side. Although not shown, the anchor may be required to rotate into and out of position so that it can pass through the shell of the steam generator. Tubelane blocking devices may also be attached to the tube.

Figure 3:
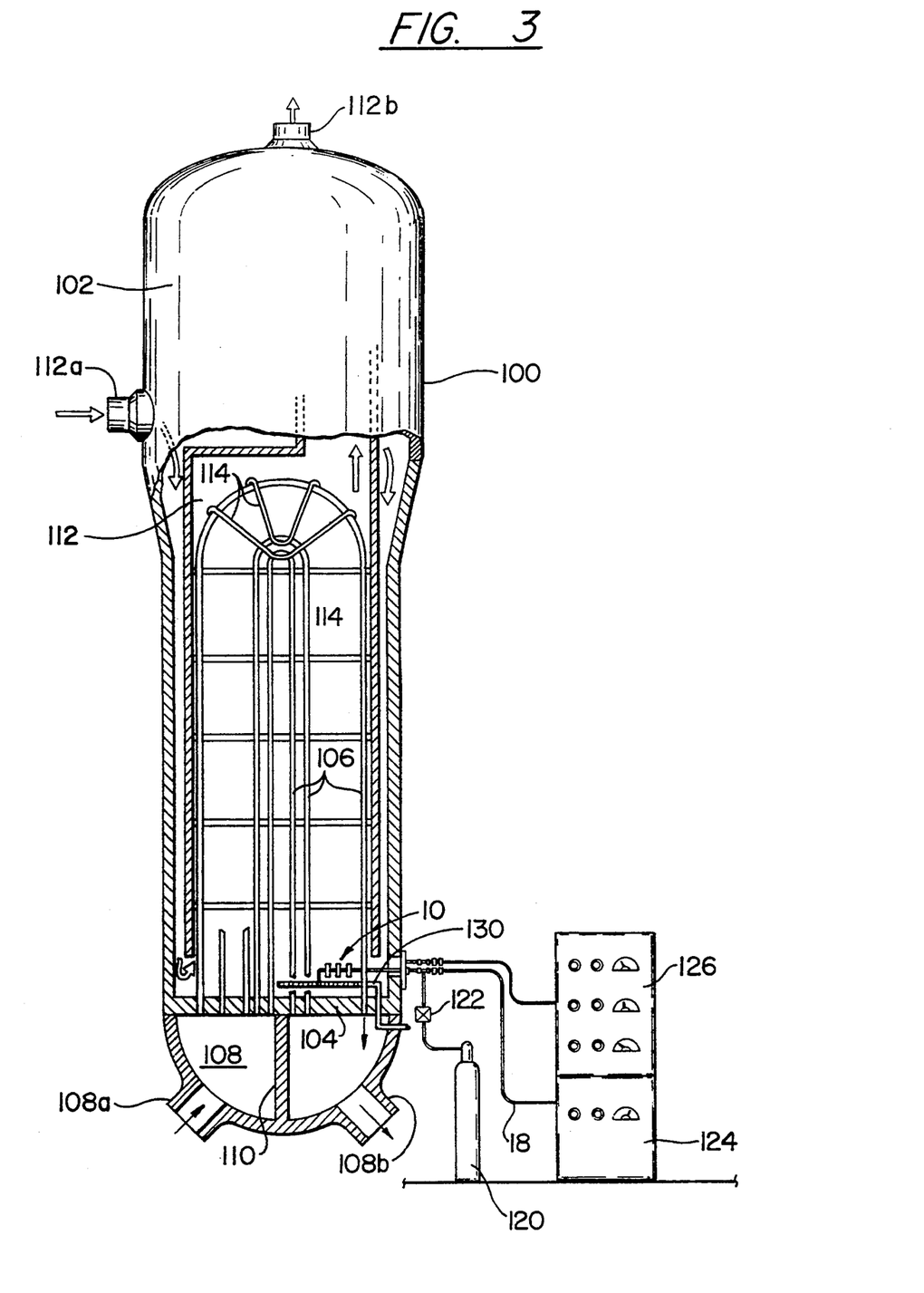
FIG. 3 displays the corrosion accelerator installed in a heat exchanger of a PWR.

Referring now to FIG. 3, the corrosion accelerator 10 is emplaced within an operating heat exchanger 100 in the form of a steam generator of a PWR. Two hydraulic flow paths, the primary and the secondary sides, are separated by a tube sheet 104, near the bottom of the pressure vessel 102, and U-tubes 106. Water from the reactor core enters the primary side 108 through inlet 108a, then circulates through the U-tubes and out of the vessel 102, returning to the core through outlet 108b. The inlets and outlets for the U-tubes 106 are isolated from each other by divider plate 110. The secondary side 112 defines a second flowpath for nonradioactive water that can contain corrosive components. Feedwater for the secondary side enters the containment vessel 102 through inlet 112a, flows down around the inner wall of the containment vessel 102, then up around and past the U-tubes lee. steam emerges from outlet 112b to drive the turbine-generator (not shown). Corrosive sludges accumulate in the crevices between the support plates 114 and the U-tubes 106. The fluid conditions (entailing fluid chemistry, flow fields and the nature of the debris carried by the fluid) experienced by the corrosion accelerator depend upon its placement. As illustrated in FIG. 3, the anchor 32 is hooked over the blowdown line 130 for support. Placement in close proximity to the heat exchange tubes 106 will more closely produce conditions experienced by the heat exchange tubes. However, as noted earlier, the accelerator can also be placed in a vessel connected to the blowdown line 130.

A pressurized gas supply 120, preferably helium, is connected to the gas inlet port. Helium is non-corrosive and provides good thermal contact between the heaters and the tube. A gas valve 122 permits simple connection and disconnection of the gas supply. Also schematically depicted in FIG. 3 is a heater control and display means 124 which connects to the heater wires 18. A person skilled in the art will be able to calibrate the heaters 14 and control the output power of the heaters to provide a desired temperature at the surface of the tube 12. Automatic controls can also be used. Also schematically depicted in FIG. 3 is a probe signal processor 126 for receiving data from the various probe means arrayed about the tube. The processing electronics are available from Capcis March, Ltd.

The corrosion accelerator can be mounted to any type of reservoir containing a corrosive medium. Although this will normally be part of a heat exchanger, such as the secondary side of a PWR steam generator, the device can be used in a laboratory setup. The crevices may be prepacked with a sludge or left clear, however, prepacking is preferred. If left clear, and monitoring probes are used, the probe surface must be electrically insulated from the tube. The end of the tube having the corrosion sites extends into the reservoir.

While the tube is in the reservoir it is pressurized with helium gas to accelerate corrosion. The pressure within the U-tubes of operating PWR steam generators is about 2200 psi, therefore, the pressure would be adjusted to at least about this level for this application. Similarly, the heaters are energized to heat the corrosion sites to at least about the temperatures experienced by the heat exchanger tubes being characterized by the device. A variety of different pressure/stress conditions can be created simultaneously if several different tubes are utilized. Higher temperatures will generate greater concentrations of corrosive chemicals at the corrosion sites because the accumulated sludges diminish the heat removal capability of the reservoir. Higher pressures cause greater stress, also accelerating corrosion. These operating temperatures and pressures will be determined by the operator.

Corrosion monitoring is accomplished either in situ with the probes or by removal of the device from the reservoir for nondestructive and/or destructive testing. If the device is mounted in a side line of the secondary side of a heat exchanger capable of being valved off from the secondary side, then the device can be removed without shutting down the heat exchanger by valving off the sideline. As mentioned above, bench-top testing of materials can also be accomplished with this invention, eliminating the heat exchanger system altogether.

Virtually the only expendable part in this device is the tube. The probes 40, the member 28, the heater assembly and the flange are all reusable. Thus, this invention provides a simple, inexpensive device for creating a corrosive condition. The methods described herein allow an operator to monitor corrosion in heat exchangers, or, if desired, to accelerate the corrosion process to be able to predict corrosive failure.

The corrosion accelerator of this invention, while having special applicability to the operation and maintenance of the heat exchangers in PWR steam generators, also has broad application to other types of fluid heat exchangers. For example, nuclear reactors used for power generation, in addition to the heat exchangers used in steam generation, have residual heat removal heat exchangers for removing heat from a reactor when the reactor is shut down. The corrosive conditions experienced by the tubes in the residual heat removal systems differs from that in the steam generator system. This apparatus and method can be utilized equally as well for the maintenance of those tubes. Heat exchangers are not unique to the nuclear power industry, and this invention can be used for characterizing corrosion in many types of heat exchanger tubing. The apparatus and methods described herein can also be useful to researchers and engineers for characterizing corrosion in a broad range of materials that are subject to corrosion.

It is understood that various modifications of this device and method may occur to those skilled in the art and it is intended that this invention be limited only by the scope of the claims.

We claim:

1. An apparatus adapted for removable insertion into a fluid heat exchanger of a pressurized water reactor containing a corrosive medium, comprising an elongated, sealed tube and means for creating a corrosion condition onthe exterior of the tube, characterized in that the means for creating a corrosion condition comprises:
    first means for providing heat to the tube at a first axial position within the tube and for pressurizing the interior of the tube with a gas;
    second means for retaining the corrosive medium in contact with the exterior surface of the tube proximate to the first axial position; and
    mounting means for remountably attaching the apparatus to a port of the heat exchanger such that the first axial position of the tube extends into the corrosive medium.

2. The apparatus at claim 1, characterized in that the first means comprises a gas inlet port for connection to a source of pressurized gas.

3. The apparatus of claim 2, characterized in that the second means comprises a member having a first surface proximate to the exterior surface of the tube forming a crevice between the first surface and the exterior surface of the tube.

4. The apparatus of claim 3, characterized in that the means for creating a corrosion condition further comprises:
    third means for providing a first signal indicative of a first corrosion condition of the exterior surface of the tube proximate to the first axial position.

5. The apparatus of claim 2, characterized in that the second means comprises a consolidated, porous material disposed adjacent to the exterior surface of the tube.

6. The apparatus of claim 5, characterized in that the means for creating a corrosion condition further comprises:
    third means for providing a first signal indicative of a first corrosion condition of the exterior surface of the tube proximate to the first axial position.

7. An apparatus adapted for removable insertion into a fluid heat exchanger of a pressurized water reactor containing a corrosive medium, comprising an elongated sealed tube and means for predicting corrosion of the heat exchanger tubes, characterized in that the means for predicting corrosion comprises:
    a gas inlet port for pressurizing the interior of the tube with a pressurized gas;
    a heater for providing heat to the tube at a first axial position within the tube;
    a structure for retaining the corrosive medium in contact with the exterior surface of the tube proximate to the first axial position;
    probe means for providing a first signal indicative of a first corrosion condition of the exterior surface of the tube proximate to the first axial position and to the structure.

8. The apparatus of claim 7, characterized in that the structure comprises a consolidated, porous material.

9. The apparatus of claim 8, characterized in that the consolidated, porous material comprises a metal oxide powder.

10. The apparatus of claim 9, characterized in that the metal oxide is a member of the group consisting of aluminum oxide, zirconium oxide and iron oxide.

11. The apparatus of claim 7, characterized in that the first signal indicative of a corrosion condition is a member of the group of signals consisting of potential noise, current noise, coupling current, zero-resistance current, ac impedance and electrochemical potential.

12. A method of predicting corrosion of exterior surfaces of heat exchange tubes within an active pressurized water reactor heat exchanger with an apparatus adapted for removable insertion within the heat exchanger comprising an elongated sealed tube, first means for heating the tube at a first axial position within the tube and for pressurizing the interior of the tube with a gas, second means for retaining a corrosive sludge in contact with the exterior surface proximate to the first axial position, and a probe for providing a first signal indicative of a first corrosion condition of the exterior surface proximate to the first axial position, comprising the steps of:

inserting a portion of the sealed tube comprising the second means within the heat exchanger;
pressurizing the interior of the tube to a first pressure;
heating the exterior surface of the tube proximate to the first axial position to a first temperature;
providing the first signal indicative of the first corrosion condition with the probe after the pressuring and heating steps.

13. The method of claim 12, characterized in that the first pressure is at least about a pressure within the heat exchange tubes of an active steam generator heat exchanger connected to the pressurized water reactor.

14. The method of claim 12, characterized in that the first temperature is at least about a temperature at the exterior surfaces of the heat exchange tubes of an active steam generator heat exchanger connected to the pressurized water reactor.

15. The method of claim 12, characterized in that the first signal indicative of the first corrosion condition is a member of the group of signals consisting of potential noise, current noise, coupling current, zero-resistance current, ac impedance and electrochemical potential.

16. A method of accelerating corrosion of surfaces contacting a corrosive medium with an apparatus adapted for removable insertion within a fluid reservoir containing the corrosive medium, comprising an elongated sealed tube, first means for providing heat to the tube at a first axial position within the tube and for pressurizing the interior of the tube with a gas, second means for retaining a corrosive sludge in contact with an exterior surface proximate to the first axial position, and third means for providing a signal indicative of a corrosion condition of the exterior surface of the tube proximate to the first axial position, comprising the steps of: first inserting a portion of the apparatus comprising the second means within the fluid reservoir;

pressurizing the interior of the tube to a first pressure;
heating the exterior surface of the tube proximate to the first axial position to a first temperature; and
providing the signal indicative of the corrosion condition with the third means.

17. The method of claim 16, characterized in that the first pressure is at least about a pressure within the heat exchanger tubes of an operating pressurized water reactor.

18. The method of claim 16, characterized in that the first temperature is at least about a temperature found within the heat exchanger tubes of an operating pressurized water reactor.

19. An apparatus adapted for removable insertion within a fluid reservoir containing a corrosive medium, comprising an elongated, sealed tube and means for creating a corrosion condition on an exterior of the tube, the means for creating a corrosion condition comprising:

first means for providing heat to the tube at a first axial position within the tube and for pressurizing the interior of the tube with a gas;
second means for retaining the corrosive medium in contact with the exterior surface of the tube proximate to the first axial position; and
third means for providing a signal indicative of a corrosion condition of the exterior surface of the tube proximate to the first axial position.

20. The apparatus of claim 19, characterized in that the second means comprises a consolidated, porous material disposed adjacent to the exterior surface of the tube.

21. The apparatus of claim 19, characterized in that the second means comprises a member having a first surface proximate to the exterior surface of the tube and forming a crevice between the first surface and the exterior surface of the tube.

* * * * *